United States Patent [19]  
van Dijk et al.

[11] 4,317,835  
[45] Mar. 2, 1982

[54] NOVEL BASIC SUBSTITUTED-ALKYLIDENAMINO-OXY-ALKYL-CARBOXYLIC ACID ESTERS

[75] Inventors: Jan van Dijk; Johannes M. A. Zwagemakers, both of Weesp, Netherlands

[73] Assignee: Duphar International Research B.V., Netherlands

[21] Appl. No.: 191,100

[22] Filed: Sep. 26, 1980

Related U.S. Application Data

[60] Division of Ser. No. 972,845, Dec. 26, 1978, Pat. No. 4,242,348, which is a continuation of Ser. No. 801,030, May 27, 1977, abandoned, which is a division of Ser. No. 509,807, Sep. 27, 1974, Pat. No. 4,044,023, which is a division of Ser. No. 151,793, Jun. 10, 1971, Pat. No. 3,853,955.

[30] Foreign Application Priority Data

Jun. 11, 1970 [NL] Netherlands ......................... 7008493  
Mar. 2, 1971 [NL] Netherlands ......................... 7102715

[51] Int. Cl.$^3$ ............................................. A61K 31/215  
[52] U.S. Cl. .................................. 424/309; 260/326.4; 260/326.43; 542/416; 546/168; 546/169; 546/170; 546/175; 546/232; 424/274; 424/246; 424/248.55; 424/250; 424/258; 424/263; 560/35  
[58] Field of Search .......................................... 424/309

[56] References Cited

U.S. PATENT DOCUMENTS 3,692,835 9/1972 van Dijk et al. .................... 564/256  
3,803,235 4/1974 van Dijk et al. .................... 564/256

*Primary Examiner*—Arthur P. Demers  
*Attorney, Agent, or Firm*—Stevens, Davis, Miller & Mosher

[57] ABSTRACT

There is disclosed pharmaceutical preparations and a method of using same in the treatment of inflammation and/or pain, e.g., treating rheumatic affections, with novel substituted alkylidene-aminooxyalkyl carboxylic acid esters.

4 Claims, 1 Drawing Figure

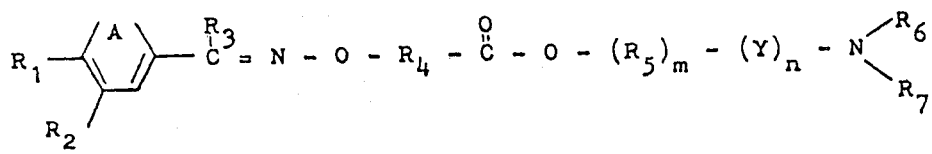 1
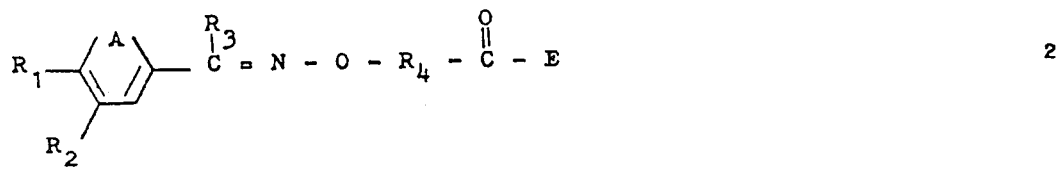 2
 3
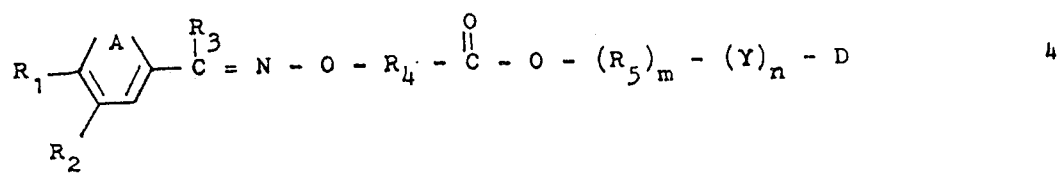 4
NHR$_6$R$_7$ 5
 6
 7
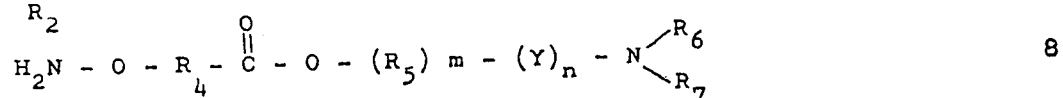 8
 9
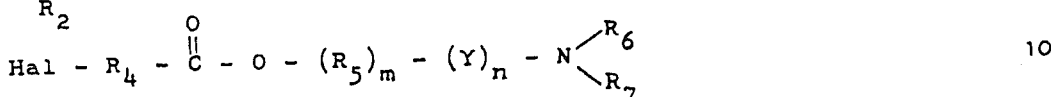 10
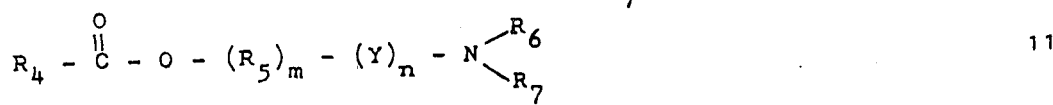 11

NOVEL BASIC SUBSTITUTED-ALKYLIDENAMINO-OXYALKYL-CARBOXYLIC ACID ESTERS

This is a division of application Ser. No. 972,845, filed Dec. 26, 1978, now U.S. Pat. No. 4,242,348, which is a continuation of Ser. No. 801,030, filed May 27, 1977, now abandoned, which was a division of Ser. No. 509,807, filed Sept. 27, 1974 and now U.S. Pat. No. 4,044,023, which is a division of Ser. No. 151,793, filed June 10, 1971, now U.S. Pat. No. 3,853,955.

The invention relates to novel basic substituted-alkylidenamino-oxylalkyl-carboxylic-acid esters.

It is known that rheumatic affections are among the most serious diseases. It is true that medicaments are known for treating these affections, but in general they have deleterious side-effects. Thus, the highly potent (N-p. chlorophenyl-5-methoxy-indolyl-3)-acetic acid has a high toxicity, so that in the last analysis the therapeutic index is low.

In the ensuing description reference is made to the sheet of drawings, wherein there is set out certain structural chemical formulea, serially numbered 1-11 for identification.

It has now been found that the novel substituted -alkylidenamino-oxyalkyl-carboxylic-acid esters of the formula 1 of the drawings and their acid-addition salts formed with pharmaceutically acceptable acids have a strong anti-inflammatory effect, a powerful analgetic activity and a low toxic effect.

Accordingly, the invention relates to novel compounds of the formula 1 and their acid addition salts formed with pharmaceutically acceptable acids, in which formula the symbols have the following meanings:

A is sulphur or the group —CH=CH—

$R_1$ is a halogen, $CF_3$ or $CH_3$, $R_2$ is a halogen, whilst $R_1$ or $R_2$ may be hydrogen, $R_3$ is hydrogen or $CH_3$, $R_4$ is a straight or a branched alkylene group containing up to 5 carbon atoms, m and n are 0 or 1 and m+n=1 or 2, $R_5$ is a straight or a branched alkylene group containing up to 6 carbon atoms which may be substituted by a phenyl group, Y is a cyclic hydrocarbon radical containing 5 or 6 carbon atoms or together with the nitrogen atom of the amino group and $R_6$ and/or $R_7$ forms a mono- or bicyclic, heterocyclic group containing at most 10 ring atoms, which group may also contain a sulphur atom as a ring atom and may be substituted by methyl, $R_6$ and $R_7$ each are hydrogen or an alkyl group containing at most 8 carbon atoms, on the understanding that together they do not contain more than 10 carbon atoms, which may be substituted by a hydroxy group, an alkoxy group containing at most 4 carbon atoms or an acyloxy group of the formula 2 (E=oxygen), $R_6$ may further be a cycloalkyl group containing from 3 to 8 carbon atoms, a phenyl, halogenophenyl or tolyl group, a phenylalkyl group containing at most 9 carbon atoms, a pyridyl group or an acyl group containing at most 10 carbon atoms, whilst $R_6$ and $R_7$ together with the nitrogen atom to which they are bound may be a mono- or bicyclic, heterocyclic group containing at most 10 ring atoms, which group may contain an oxygen atom or a second nitrogen atom as a ring atom.

Because of their properties the compounds according to the invention may be used for treating rheumatoid arthritis, Bechterew disease, arthitis psoriatica, collagen disease, serious osteoarthrosis, acute lumbago, humeroscapular periarthritis, acute sterile non-infected bursitis, thrombophlebitis and acute rheumatic polyarthritis and the like.

The dosage in which and the frequency at which the compounds are to be administered for treating these affections depend on the seriousness of the affections. As a rule, however, the physician treating the patient will have no difficulty in arriving at the right treatment. In general, from 50 to 1000 mg daily will be administered to the patient and such a dosis may be divided into several portions. As a rule, from 100 to 500 mg daily will be sufficient.

The anti-inflammatory effect of the compounds was determined by the carragheenin test carried out according to a modification of the method of Winter, Risley and Nuss, Proc. Soc. Exp. Biol. 111-544 (1962).

In this test the reduction of the edema produced by carragheenin is used as a measure of the anti-inflammatory activity.

The test was made with male rats, weight about 220 g. The animals were made to fast for the 16 hours preceding the test. The substance to be tested is suspended in a 1% tragacanth solution and administered orally. The administration of the substance is immediately followed by water loading up to 5 ml per animal. 1 hour after the administration of the test substance and the water loading, 0.5 ml of a 1½% carragheenin solution is injected intraplantarly and the thickness of the legs (dorsal-plantar distance) is determined by means of a micrometer.

3 hours after the administration of the carragheenin the thickness of the edema produced is determined. The swelling of the leg is expressed as a percentage relative to the zero hour value. The percentage of the inhibition is calculated according to the relation $$\frac{\% \text{ blank} - \% \text{ test group}}{\% \text{ blank} - 100} \times 100\%.$$

From the results of the series of dosages an $ED_{50}$ value was computed. This is the dosage which causes a 50% reduction of the edema.

The analgetic activity of the compounds was determined according to a modification of the method of Randall and Sellito (Arch. Int. Pharmacodyn. 109-40-9—(1957)).

The diminution of the response to pain due to the increasing pressure on a rat's leg inflamed by means of yeast serves as a criterion for the analgetic effect.

The test is performed on male rats having weights between 100 and 130 g. One hour before the administration of the test preparation the animals are intraplantarly injected with 0.1 ml of a 20% yeast suspension. The compounds to be tested are suspended in a 1% tragancanth solution and administered orally. One hour, two hours and four hours after the administration of the test substance the pain threshold is measured with increasing pressure on the inflamed leg.

As a control the pain reactions of a group of animals which have not been treated with the pharmacon are determined.

The results are expressed as a percentage of the mean blank value.

From the results of a series of dosages an $ED_{50}$ value was computed, i.e. the dosage which produces a 100% rise of the pain threshold.

The compounds according to the invention can be prepared by known methods.

Accordingly the invention also relates to a method of producing new basic substituted-alkylideneamino-oxy-alkyl-carboxylic-acid esters, which is characterized in that compounds of the general formula 1 are prepared by methods known for preparing compounds of this type and by analogous methods.

The compounds according to the invention are obtainable, for example, by reacting a compound of the formula 2, in which the symbols have the same meanings as in the formula 1 and E is a chlorine atom, a methoxy or a hydroxy group, with a compound of the formula 3, in which the symbols have the same meanings as in the formula 1 and B is a hydroxy group or a halogen atom, in which latter case E is a hydroxy group or a salt thereof. The reaction is preferably performed in an inert solvent, such as dimethylformamide, N-methylpyrrolidone, benzene and the like, at temperatures between 0° C. and about 100° C. When primary and secondary amines of the formula 3 are reacted and E is a chlorine atom the reaction is preferably carried out under acid conditions.

Compounds according to the invention in which Y does not form a heterocyclic group with the nitrogen of the amino group may also be produced by reacting a compound of the general formula 4 with a compound of the general formula 5, in which formulae the symbols have the same meanings as in the formula 1 and D is a halogen atom or a tosyloxy group. This reaction also is preferably carried out in an inert solvent, for example one of the aforementioned solvents. As a rule the reaction temperature lies between room temperature and the boiling point of the solvent.

The compounds of the formula 4 are obtainable by reacting an acid chloride of the formula 2 (E=Cl) with a compound of the formula 6, where D has the same meaning as in formula 4.

Another method of producing compounds of the formula 1 is to react a compound of the formula 7 with a compound of the formula 8, in which formulae the symbols have the same meanings as in the formula 1. This reaction is preferably performed in an inert solvent, such as dimethylformamide, dimethylsulfoxide, alcohols and the like, at temperatures between room temperature and the boiling point of the reaction mixture.

The compounds of the formula 8 may be obtained by acid hydrolysis from the corresponding oxime derived from acetone. The latter compound may be obtained by one of the afore-described methods.

Furthermore, the novel compounds may be obtained by reacting a compound of the formula 9 with a compound of the formula 10, in which formulae the symbols have the same meanings as in the formula 1, whilst in the formula 9 M represents a metal atom or a hydrogen atom. The reaction is carried out in an inert solvent, such, for example, as alcohols, dimethylsulfoxide, dimethylformamide and the like. As a rule the reaction is performed at a temperature between room temperature and the boiling point of the solvent. If in the formula 9 M is a hydrogen atom, an acid binder is preferably added.

An alternative method of producing compounds of the formula 1, where $R_4$ is an alkylene group containing from 2 to 5 carbon atoms, is to react a compound of the formula 9 with a compound of the formula 11, in which formulae the symbols have the same meanings as in the formula 1 and $R'_4$ is an alkenyl group containing from 1 to 5 carbon atoms. In this reaction the symbol M in formula 9 is hydrogen. The reaction is carried out at temperatures between room temperature and the boiling point of the mixture in an inert solvent, for example an alcohol.

Suitable acids with which the amines of the formula 1 may form addition salts are pharmaceutically acceptable organic and inorganic acids such, for example, as halogen hydrogen acids, sulphuric acid, phosphoric acid, tartaric acid, malic acid, citric acid, maleic acid, succinic acid, acetic acid, propionic acid, palmitic acid, benzoic acid, fumaric acid, p.toluenesulphonic acid, and an algetically active acids, such as acetylsalicylic acid, phenylacetic acid and the like.

Examples of acyl(oxy) groups which may be found in $R_6$ and $R_7$ are acetyl(oxy) and (p.Cl. α-methylbenzylidene) aminooxy-acetyl(oxy).

The compounds according to the invention may be made up into pharmaceutical preparations such, for example, as tablets, pills, powders, injection liquids, salves, suppositories, dragees and the like by known methods. Hence, the invention also relates to the production of pharmaceutical preparations and to the preparations themselves.

As carrier materials the substances commonly used in pharmaceutics may be employed.

The invention will now be described more fully with reference to the following Examples.

{[(4-chloro-α-methylbenzylidene)amino]oxy}acetic acid (2-acetamidoethyl)ester

A solution of 2.57 g 2-acetamidoethanol in a mixture of 15 ml of benzene, 10 ml of dioxan and 15 ml of dimethylformamide was mixed with 2.01 ml of pyridine. The mixture was added with stirring at room temperature to a solution of 6.15 g of {[(4-chloro-α-methylbenzylidene)amino]oxy}acetylchloride in 50 ml of benzene. The mixture was allowed to stand overnight at room temperature and then mixed with 10 ml of water. The water layer was separated from the organic layer. The organic layer was successively washed with 2 10 ml-portions of water, 3 10 ml-portions of a saturated sodiumbicarbonate solution and 3 10 ml-portions of water. The solution was then dried over anhydrous sodiumsulphate and evaporated to dryness in a vacuum. The residue was taken up in 50 ml of benzene, from which the aforementioned substance crystallized. Melting point 112°–114° C.

2.

N-methyl-2,2'bis[2-{[4-chloro-α-methylbenzylidene)amino]oxy}acetoxy]diethylamine. HCl A solution of 9.8 g of {[(4-chloro-α-methylbenzylidene)amino]oxy}acetylchloride in 50 ml of benzene was mixed whilst cooling with a solution of 2.38 g of N-methyl-2,2'-dihydroxydiethylamine and 5.55 ml of triethylamine in 50 ml of benzene. The mixture was allowed to stand at room temperature for three days and then mixed with 50 ml of water. After the organic liquid had been separated off, it was washed with 2 50 ml-portions of water, 3 50 ml-portions of a saturated sodium bicarbonate solution and 3 25 ml-portions of water. After drying over anhydrous sodiumsulphate the solution was evaporated to dryness in a vacuum. The residue was taken up in 10 ml of ethanol. The solution was neutralized with ethanolic hydrochloric acid and diluted with 100 ml of anhydrous diethylether. The above-mentioned substance crystallized out, was filtered off, washed with diethylether and recrystallized from 300 ml of benzene. Melting point 82°–83° C.

3. (4-Chloro-α methylbenzylidene)amino-oxyacetic acid(2-dimethylamino-ethyl)ester hydrochloride 4.3 g of 2-chloro-N,N-dimethyl ethylamine was added to a suspension of 10 g of the sodium salt of (4-chloro-α-methylbenzylidene)amino-oxyacetic acid in 30 ml of dimethylformamide. The mixture was stirred for 72 hours. It was then diluted with water and extracted with diethylether. The resulting ethereal solution was extracted with 20 ml of 2 N hydrochloric acid. The acid extract was then made basic with 30 ml of 2 N sodium hydroxide and extracted with diethylether. The latter ethereal extract was washed, dried over anhydrous sodium sulphate and after concentration by evaporation neutralized with alcoholic hydrochloric acid. When diethylether was added the hydrochloride of the (2-dimethyl-aminoethyl)ester of (4-chloro-α-methylbenzylidene) aminooxyacetic acid crystallized out. It was recrystallized from an alcohol-ether mixture; melting point 160°–162° C. with decomposition.

4. (2-Dimethylaminopropyl)ester of (4-chloro-α-methylbenzylidene)amino-oxyacetic acid hydrochloride A solution of 2.3 g of (4-chloro-α-methylbenzylidene)-amino-oxyacetic acid in 10 ml of benzene was converted into a solution of the acid chloride by boiling it with 0.60 ml of thionylchloride under a reflux condenser for about 20 minutes. The solvent was then removed in a vacuum and the acid chloride was dissolved in about 12 ml of benzene.

This solution was mixed, whilst cooling with ice, with a solution of 2.09 g of 2-dimethylaminopropanol in 20 ml of benzene. After the mixture had been allowed to stand overnight at room temperature it was mixed with about 40 ml of a 5% sodiumbicarbonate solution and about 20 ml of ether. The mixture was separated and the organic phase was washed several times with 10 ml-portions of water, until the washing liquid became neutral. The washed solution was then dried over anhydrous sodiumsulphonate, after which the solvents were removed in a vacuum. The residue, the (2-dimethylaminopropyl)ester of (4-chloro-α-methylbenzylidene) aminooxyacetic acid, was neutralized with 2 N alcoholic hydrochloric acid and the resulting hydrochloride was crystallized by adding diethyl ether to the solution. The substance was recrystallized from a 10-fold amount of benzene and then dried in a vacuum at 100° C. beside phosphorus pentoxide. Melting point of the hydrochloride: 118°–119° C.

5. (2-methylamino-ethyl)ester of (4-chloro-α-methylbenzylidene)amino-oxyacetic acid hydrochloride A solution of 2.79 g of the hydrochloride of 2-(methylamino)ethanol in 50 ml of dimethylformamide was mixed with a solution of 6.15 g of (4-chloro-α-methylbenzylidene)amino-oxyacetylchloride (prepared according to Example 2) in 30 ml of benzene. The mixture was allowed to stand at room temperature for 48 hours and then the solvents were distilled off in a vacuum. The residue was mized with 50 ml of water and 50 ml of diethylether and, after all had been dissolved, the layers were separated. The aqueous solution was extracted with 2 50 ml-portions of diethylether, made alkaline by an excess of 2 N sodiumhydroxide and reextracted with 3 50 ml-portions of diethylether. The latter ethereal extract was washed with 3 15 ml-portions of water and then dried over anhydrous sodiumsulphate. The ether was distilled off in a vacuum and the residue was neutralized with 2 N alcoholic hydrochloric acid. When ether was added to the neutralized solution the hydrochloride of the (2-methylaminoethyl)ester of (4-chloro-α-methylbenzylidene) amino-oxyacetic acid crystallized out. Melting point 180°–182° C.

6. (2-amino-ethyl)ester of (4-chloro-α-methylbenzylidene)amino-oxyacetic acid hydrochloride A solution of 1.2 g of (4-chloro-α-methylbenzylidene) amino-oxyacetyl chloride in 3 ml of benzene was added whilst stirring to a solution of 0.45 g of the hydrochloride of 2-aminoethanol in 10 ml of dimethylformamide. After the reaction mixture had been allowed to stand at room temperature for 24 hours it was mixed with 25 ml of diethylether and 25 ml of a 10% solution of potassium bicarbonate. On termination of the carbondioxide evolution the mixture was separated and the ethereal layer was washed another time with 10 ml of water. The ethereal solution was extracted with 6 ml of 2 N-hydrochloric acid and then twice with altogether 15 ml of water. The latter three extracts were combined and mixed with 2 g of potassium bicarbonate. On termination of the evolution of carbon dioxide the mixture was twice extracted with diethylether. The ethereal extracts were dried with anhydrous sodiumsulphate, concentrated by evaporation and then neutralized with 2 N alcoholic hydrochloric acid. The addition of ether to the neutralized solution resulted in the crystallisation of the hydrochloride of the (2-aminoethyl)ester of (4-chloro-α-methylbenzylidene) aminooxyacetic acid. Melting point 167°–169° C. with decomposition.

The following HCl salts (see formule 1) were also obtained by the method of Example 4.

| $R_1$ | $R_2$ | A | $R_3$ | $R_4$ | $R_5$ | $R_6$ | $R_7$ | melting point °C. |
|---|---|---|---|---|---|---|---|---|
| Cl | H | CH=CH | $CH_3$ | $CH_2$ | $CH(CH_3)CH_2$ | $CH_3$ | $CH_3$ | 149–150 |
| Cl | H | CH=CH | $CH_3$ | $CH_2$ | $(CH_2)_2$ | $C_2H_5$ | $C_2H_5$ | 128–129.5 |
| Cl | H | CH=CH | $CH_3$ | $CH_2$ | $(CH_2)_3$ | $CH_3$ | $CH_3$ | 159–160 |
| Cl | H | CH=CH | $CH_3$ | $CH_2$ | $(CH_2)_2$ | —$(CH_2)_5$— | | 167–169 |
| Cl | H | CH=CH | $CH_3$ | $CH_2$ | $(CH_2)_2$ | —$(CH_2)_2$—O—$(CH_2)_2$— | | 159–162 |
| Cl | H | CH=CH | $CH_3$ | $CH_2$ | $(CH_2)_2$ | —$(CH_2)_4$— | | 163–165 |
| Cl | H | CH=CH | $CH_3$ | $CH_2$ | $(CH_2)_2$ | $CH_3$ | $C_6H_5$ | 144–147 |
| F | H | CH=CH | $CH_3$ | $CH_2$ | $(CH_2)_2$ | $CH_3$ | $CH_3$ | 147–149 |
| Br | H | CH=CH | $CH_3$ | $CH_2$ | $(CH_2)_2$ | $CH_3$ | $CH_3$ | 180–182 |
| Cl | Cl | CH=CH | $CH_3$ | $CH_2$ | $(CH_2)_2$ | $CH_3$ | $CH_3$ | 167–168 |

-continued

| R₁ | R₂ | A | R₃ | R₄ | R₅ | R₆ | R₇ | melting point °C. |
|---|---|---|---|---|---|---|---|---|
| CH₃ | H | CH=CH | CH₃ | CH₂ | (CH₂)₂ | CH₃ | CH₃ | 163-165 |
| Cl | H | CH=CH | CH₃ | (CH₂)₃ | (CH₂)₂ | CH₃ | CH₃ | 106-108 |
| *Cl | H | CH=CH | CH₃ | CH₂ | (CH₂)₂ | C₆H₁₁ | H | 172-174 |
| Cl | H | CH=CH | H | CH₂ | (CH₂)₂ | CH₃ | CH₃ | 164.5-166 |
| Cl | H | —S— | CH₃ | CH₂ | (CH₂)₂ | CH₃ | CH₃ | 174-175.5 |

The compounds marked with an asterisk in the Table are free bases. In these compounds the neutralisation step using ethanolic hydrochloric acid was not employed.

TABLET 200 g of {[(α-methyl-4-chlorobenzylidene)amino]oxy}acetic acid (1-methyl-2-dimethylamino)ethylester hydrochloride was mixed with 190 g of sec. calciumphosphate, 90 g of microcrystalline cellulose and 120 g of a mixture consisting of 200 parts of maize starch, 32 parts of talc and 4 parts of magnesium stearate, until the mixture was homogeneous. From this mixture tablets each having a diameter of 13 mm and a weight of 600 mg were struck.

SUPPOSITORY 100 mg of {[(α-methyl-4-chlorobenzylidene)amino]oxy}acetic acid (2-methylamino)ethylesterhydrochloride was formulated with 1.5 g of suppository material into a suppository.

INJECTION LIQUID 100 g of {[(α-methyl-4-bromobenzylidene)amino]oxy}acetic acid (2-dimethylamino)ethylester hydrochloride was mixed with 15 g of benzylalcohol. The solution was then made up to a volume of 1,000 ml with distilled water. It was then strained through a bacterial filter, after which ampoules of 1 or 2 ml were aseptically filled with the liquid.

2-(N-morpholino)-ethyl ester of {[(4-chloro-α-methylbenzylidene)amino]oxy}acetic acid A mixture of 14.5 g (2-chloroethyl)ester of [{(4-chloro-α-methylbenzylidene)amino}oxy]acetic acid, obtained by reacting equimolecular amounts of 2-chloroethanol and [{(4-chloro-α-methylbenzylidene)amino}oxy]acetylchloride and pyridine in benzene, and 8.6 g of morpholine was heated on a water bath for 5 hours. After cooling, the reaction mixture was mixed with water and diethylether and then with 70 ml of saturated sodium bicarbonate solution. The layers were separated and the water layer was extracted twice with ether. The combined ethereal extracts were washed twice with 30 ml-portions of saturated sodium bicarbonate solution and then thrice with 50 ml-portions of water. The washed ethereal solution was dried over anhydrous sodium sulfate and then concentrated in vacuo. The concentrate was dissolved in a fivefold amount of ethanol and subsequently neutralized with 2 N alcoholic hydrochloric acid. The hydrochloride of the superscribed substance crystallized out. It was drawn off and recrystallized from a 4-fold amount of ethanol. Melting point 159°–162° C.

(N-ethyl-3-piperidyl)ester of {[(4-chloro-α-methylbenzylidene)amino]oxy}acetic acid hydrochloride A solution of 0.74 g of the dihydrochloride of the (N-ethyl-3-piperidyl)ester of 2-aminooxyacetic acid in 9 ml of absolute ethanol was mixed with 0.52 g of 4'-chloroacetophenone and then with a solution of 0.33 g of sodium acetate in 0.50 ml of water.

After the reaction mixture had been allowed to stand overnight the solvent was removed in vacuo. The residue was mixed with a small amount of water and the resulting solution was then extracted twice with a diethyl ether/petroleum ether mixture 1:1. Subsequently the aqueous solution was mixed with 9 ml of saturated sodium bicarbonate solution, and the mixture was extracted thrice with portions totalling 40 ml of diethyl ether. The ethereal solution was dried over anhydrous sodium sulfate. The dried solution was neutralized with alcoholic hydrochloric acid, with the result that the hydrochloride of the superscribed substance was precipitated and crystallized slowly. Melting point 160° C.

{(3-pyridyl)methyl}ester of {[(4-chloro-α-methylbenzylidene)amino]oxy}acetic acid A solution of 5.3 ml of chloroacetyl chloride in 40 ml of benzene was added drop by drop with stirring to a solution of 5.52 g of 3-(hydroxymethyl)pyridine in 40 ml of pyridine. The reaction mixture was stirred 3 hours at this temperature and then half an hour at room temperature. The resulting precipitate was removed by drawing off and the clear solution was evaporated in vacuo to a residue of about 18 g. This residue was mixed with 50 ml of ice water and then extracted thrice with portions totalling 200 ml of benzene. The benzene solution was washed with 4 portions totalling 60 ml of ice water and then dried over anhydrous sodium sulfate. The solvent was subsequently largely distilled off in vacuo at 30°–40° C. 5.6 g of the resulting residue, which consisted of 3-[(2-chloroacetoxy)methyl]pyridine was immediately mixed with 5.1 g of 4'-chloroacetophenone oxime and 30 ml of dimethyl formamide. To the resulting solution 1.3 g of powdered sodium hydroxide was slowly added at 0° C. with stirring. The mixture was stirred half an hour at 0° C. and then 2 hours at room temperature. After 1 ml of acetic acid had been added the mixture was allowed to stand at 0° C. for 14 hours. The reaction mixture was then evaporated in vacuo and the concentrate was mixed with 140 g of an ice/water mixture and 100 ml of benzene. The layers were separated and the water-containing layer was washed twice with benzene. The combined benzene extracts were washed with 50 ml of 0.5 molar sodium bicarbonate solution and thrice with water. The washed benzene abstracts were concentrated in vacuo, after which by-products were chromatographically removed by means of a silicagel column and methylene chloride + 5% by volume of acetone as the eluant. The superscribed substance crystallized out. Melting point 60.5°–62.5° C.

We claim:

1. A pharmaceutical preparation for the treatment of inflammation and/or pain comprising a pharmaceutical effective anti-inflammatory and/or analgesic amount of a compound of the formula:

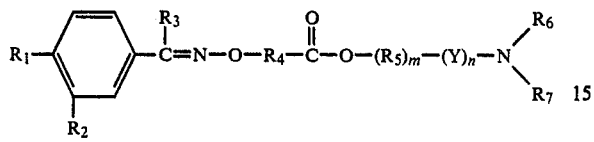

wherein $R_1$ is a moiety selected from the group consisting of hydrogen, halogen, $CF_3$ and $CH_3$, $R_2$ is a moiety selected from the group consisting of chlorine and hydrogen, $R_3$ is a moiety selected from the group consisting of hydrogen and $CH_3$, $R_4$ is alkylene of up to 5 carbon atoms, m and n are each 0 or 1 and m+n is 1 or 2, $R_5$ is alkylene of up to 6 carbon atoms which may be substituted by phenyl, Y is a cyclic hydrocarbon radical of 5 or 6 carbon atoms, $R_6$ is a moiety selected from the group consisting of hydrogen, alkyl of up to 8 carbon atoms, cycloalkyl of 3 to 8 carbon atoms, phenyl, tolyl, and acetyl and (p.chloro α-methylbenzylidene) aminooxyacetyl, and $R_7$ is a moiety selected from the group consisting of hydrogen, alkyl of up to 8 carbon atoms, alkyl of up to 8 carbon atoms substituted with hydroxyl with the proviso that when $R_6$ and $R_7$ are each alkyl or hydroxy substituted alkyl, $R_6$ and $R_7$ together do not contain more than 10 carbon atoms and the acid addition salts thereof with pharmaceutically acceptable acids and a liquid or finely divided solid carrier material therefor.

2. A method of treating a patient having inflammation and/or pain comprising administering to a patient having inflammation and/or pain the pharmaceutical preparation of claim 1.

3. The method of claim 2 wherein said compound is administered at a dose of 50 to 1,000 mg daily.

4. The preparation of claim 1 wherein said compound is {[(4-chloro-α-methylbenzylidene)amino]oxy}-acetic acid (2-dimethylamino-ethyl) ester or an acid addition salt thereof with a pharmaceutically acceptable acid.

* * * * *